(12) United States Patent
Ljungmann et al.

(10) Patent No.: US 8,409,506 B2
(45) Date of Patent: Apr. 2, 2013

(54) APPARATUS FOR EXECUTION OF TREATMENT OPERATIONS IN CONNECTION WITH COLOURING OF TISSUE SPECIMENS ON OBJECT GLASSES

(71) Applicant: Dako Instrumec AS, Oslo (NO)

(72) Inventors: Oystein Ljungmann, Ski (NO); Torstein Ljungmann, Nesoddtangen (NO)

(73) Assignee: Dako Instrumec AS, Olso (NO)

( * ) Notice: Subject to any disclaimer, the term of this patent is extended or adjusted under 35 U.S.C. 154(b) by 0 days.

(21) Appl. No.: 13/654,259

(22) Filed: Oct. 17, 2012

(65) Prior Publication Data

US 2013/0040339 A1 Feb. 14, 2013

Related U.S. Application Data

(63) Continuation of application No. 12/162,850, filed as application No. PCT/NO2007/000031 on Jan. 31, 2007, now Pat. No. 8,318,095.

(30) Foreign Application Priority Data

Feb. 2, 2006 (NO) .................................. 2006 0555

(51) Int. Cl.
*G01N 21/00* (2006.01)
(52) U.S. Cl. ............... 422/65; 422/63; 422/64; 422/66; 422/67; 422/50; 422/500; 436/180
(58) Field of Classification Search .............. 422/63–67, 422/50, 500; 436/180
See application file for complete search history.

(56) References Cited

U.S. PATENT DOCUMENTS

| | | | | |
|---|---|---|---|---|
| 4,741,043 A | * | 4/1988 | Bacus | 382/129 |
| 6,076,583 A | * | 6/2000 | Edwards | 156/539 |
| 2004/0009098 A1 | * | 1/2004 | Torre-Bueno | 422/63 |

FOREIGN PATENT DOCUMENTS

| | | |
|---|---|---|
| JP | 2002-541494 | 12/2002 |
| JP | 2003-156419 | 5/2003 |
| JP | 2005-527811 | 9/2005 |
| WO | WO 00/37986 | 6/2000 |
| WO | WO 00/62035 | 10/2000 |
| WO | WO 2004/059441 | 7/2004 |
| WO | WO 2006/068500 | 6/2006 |

* cited by examiner

*Primary Examiner* — Jyoti Nagpaul
(74) *Attorney, Agent, or Firm* — Finnegan, Henderson, Farabow, Garrett & Dunner LLP

(57) ABSTRACT

An apparatus for automatic execution of different treatment operations in connection with staining of tissue specimens on microscope slides, wherein the apparatus (1) comprises a loading station (2) for microscope slides (7) with tissue specimens, a number of reagent stations (3) for staining of the tissue specimens on supplied microscope slides, a conveyor (5) for transfer of microscope slides (7) between the stations (3) in accordance with a staining program, an unloading station (10) for treated microscope slides, and a control unit (19) for controlling the treatment operations in accordance with a data program. The apparatus comprise a photo station (25) with a digital camera (26) for automatic photographing with a background light source of the finished treated tissue specimens on supplied microscope slides (7). The camera is connected to the control unit (19) of the apparatus and the control unit is arranged to store the picture of each individual tissue specimen and information which is located on the relevant microscopic slide (7) and preferably also information about the staining program and status of reagents at the reagent stations (3) for automatic transmission of the information to a place for result analysis.

10 Claims, 1 Drawing Sheet

Figure 1:
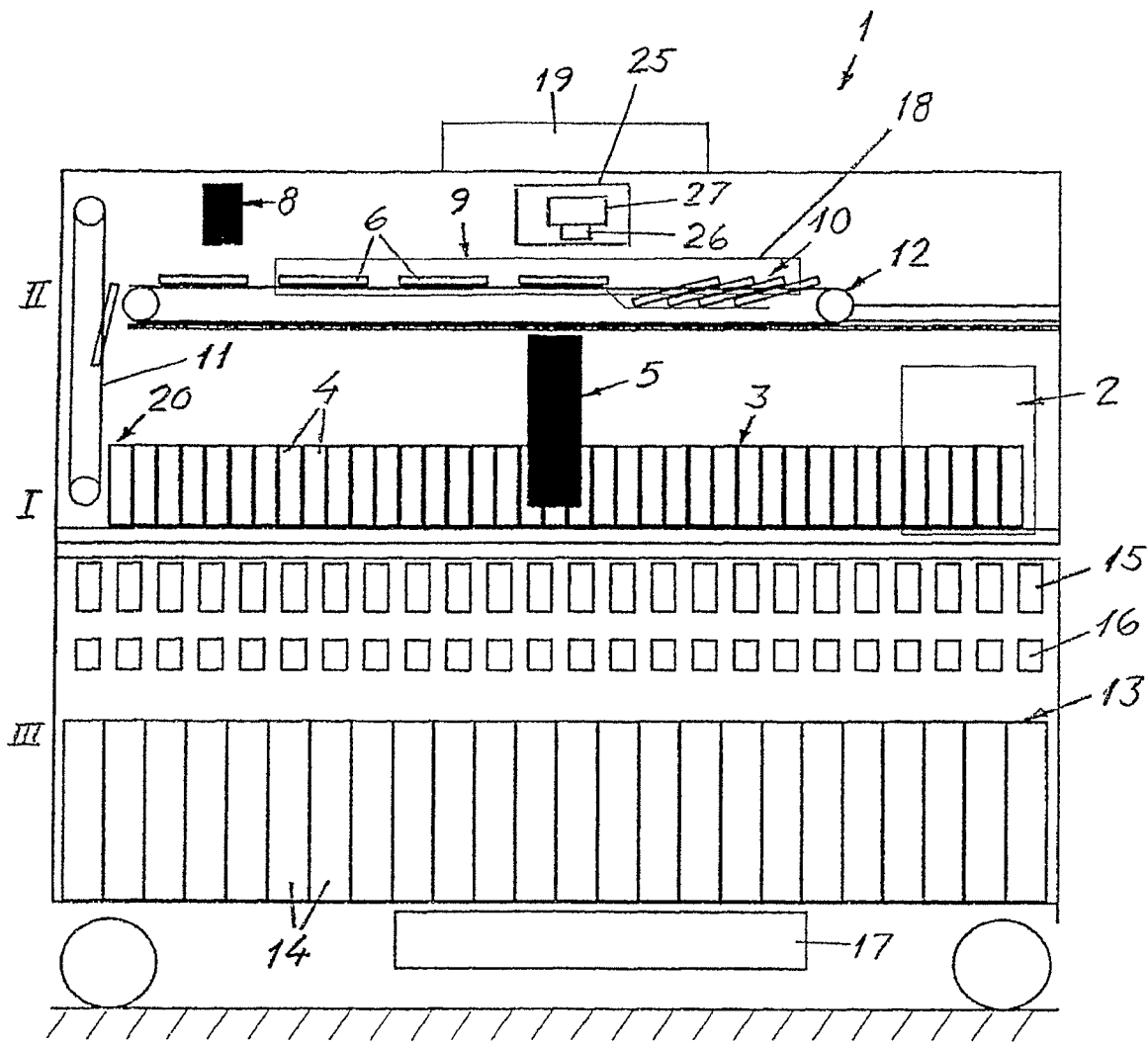

APPARATUS FOR EXECUTION OF TREATMENT OPERATIONS IN CONNECTION WITH COLOURING OF TISSUE SPECIMENS ON OBJECT GLASSES

This application is a continuation of U.S. application Ser. No. 12/162,850, filed Oct. 14, 2008, which is a National Stage Entry of International Patent Application No. PCT/NO07/00031, filed Jan. 31, 2007, and which claims priority benefits from Norwegian Patent Application No. 2006 0555, filed Feb. 2, 2006, which are incorporated herein by reference.

The invention relates to an apparatus for automatic execution of different treatment operations in connection with staining of tissue specimens on microscope slides, wherein the apparatus comprises a loading station for microscope slides with tissue specimens, a number of reagent stations for staining of the tissue specimens on supplied microscope slides, a conveyor for transfer of microscope slides between the stations in accordance with a staining program, an unloading station for treated microscope slides, and a control unit for controlling the treatment operations in accordance with a data program.

An apparatus of the above-mentioned type is shown and described in Norwegian patent application No. 2004 5622. With such an apparatus many different treatment operations can be executed, such as initial fixing of paraffin casted tissue specimens on microscope slides, staining of tissue specimens on microscope slides, mounting of cover glasses on the stained tissue specimens microscope slides, and drying of stained tissue specimens microscope slides after application of glue and mounting of cover glasses, in accordance with a selected programmed running process.

After the current treatment operations of the said type have been executed, the microscope slides are according to usual practice today subjected to manual microscoping. This treatment comprises also manual loading of photo equipment for taking pictures of the tissue specimens with a view to result analysis (so-called "screening"). By the manual microscoping, it must be waited 24 hours after the application of the cover glasses so that the specimens no longer liberate much dissolvent gasses. Additionally that the manual handling is comparatively time consuming it may also be exposed to human error, e.g. due to erroneous registration or mixed up patient data.

A main object of the invention is to provide an apparatus of the current type, which is able to store all information about each specimen without any source of error, in such a way that a 100% quality assurance of the specimen results is obtained.

An additional object of the invention is to provide an apparatus, which makes it possible, that the specimens can be studied essential faster than with manual microscoping, which means an essential labour saving for a user.

The above-mentioned objects are achieved by means of an apparatus of the introductorily stated type, which, according to the invention, is characterised in that the apparatus comprise a photo station with a digital camera for automatic photographing with a background light source of the finished treated tissue specimens on supplied microscope slides, the camera is connected to the control unit of the apparatus and the control unit is arranged to store the picture of each individual tissue specimen and information which is located on the relevant microscopic slide and preferably also information about the staining program and status of reagents at the reagent stations for automatic transmission of the information to a place for result analysis.

Preferable embodiments are stated in the dependent claims.

Figure 2:
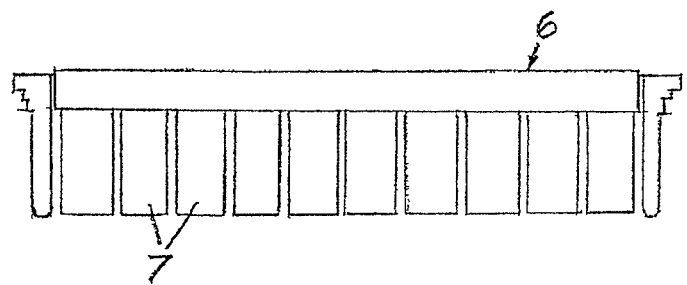

The invention will now be further described by means of an exemplary embodiment with reference to the drawings, wherein FIG. 1 shows a schematic side view of an apparatus according to the invention, and FIG. 2 shows a plan view of a carrier device for microscope slides for use in the apparatus shown in FIG. 1.

In FIG. 1 it is shown an apparatus corresponding to the apparatus which is shown and described in the previously mentioned Norwegian patent application No 2004 5622 which additionally is provided with a photo station according to the present invention. In the following a brief description of the structure of the apparatus shall be given. For a further description of the apparatus and its manner of operation, reference is made to the said patent application.

The apparatus 1 shown in the drawing comprises three levels I, II and III, having units for execution of the relevant treatment operations.

The first level I includes a loading and preheating station 2 for microscope slides, a number of reagent stations 3 consisting of vessels 4 with reagents for staining of tissue specimens on microscope slides, and a conveyor 5 for transfer of carriers/holding devices 6 with microscope slides 7, (see FIG. 2) from vessel to vessel in accordance with a selected staining/data program.

The second level II includes a station 8 for application of cover glasses (not shown) on the stained microscope slides, a succeeding drying station 9 and a storing/unloading station 10 for the ready-treated microscope slides. In the illustrated embodiment, the second level II is located above the first level I, and a hoist or lifting means 11 is provided for transfer of carriers 6 with stained microscope slides from the first level to the cover glass applying station 8 on the second level. A horizontal transport means 12 is provided for transfer of carriers 6 with microscope slides 7 through the cover glass applying station 8 and the drying station 9 to the unloading station 10.

The third level III, which is located below the first level 1, includes an assembly 13 of a number of storage tanks 14 for the relevant reagent liquids, wherein the tanks are connected to the appurtenant vessel 4 at the reagent stations 3 via connecting lines (not shown) on which there are arranged pumps 15 for the supply of liquid to the vessels, and moreover filers 16 for filtering of the liquids.

The apparatus is also shown to include a filter/blower unit 17 for ventilation of the apparatus. This unit is in communication with a vent inlet 18 at the top of the apparatus, and thereby provides for transport and blowout of venting air through the apparatus. In this manner, the whole apparatus is ventilated, so that i.a. dangerous fumes from the reagent stations are removed in a justifiable manner.

The apparatus also includes an electronic control unit which is symbolically shown as a block 19, and which takes care of controlling the treatment operation of the apparatus in accordance with a data program. Further, the apparatus comprises a control panel (not shown) for operation and working of the apparatus. This panel includes a number of touch or contact keys (control keys and working keys), and also a display giving information about the status etc. of the apparatus during the operation.

The means 11 for gripping and transfer of carriers is only schematically shown in FIG. 1, and consists of a hoist for lifting of the carriers in the dedicated transfer area 20 to the second level II. As an alternative to such a lifting means, the transfer means may be arranged at the second level and arranged to fetch carriers 6 from the area 20 to the second level.

The station 8 for application of cover glasses on the stained microscope slides is also only schematically shown in FIG. 1. This station includes a number of elements, more specifically a cover glass magazine with a dispenser function, a glue pump, a glue dispenser and a unit for mounting of cover glasses on the supplied microscope slides with stained tissue specimens. Further, the station contains a detection unit for detection of microscope slides arriving at the station in the different supplied carriers. The cover glass magazine advantageously may be constructed for delivering cover glasses laterally from the bottom of the magazine. For a further description of such a station reference may e.g. be made t the international patent application No. PCT/NO99/00396 (WO 00/37986).

For a further description of the carrier device/carrier 6 reference is made to the previously mentioned Norwegian patent application and also the Norwegian patent application 2004 5625.

In accordance with the invention the above-described apparatus is provided with a photo station 25 on which it is arranged a digital camera for automatic photographing with a background light source of the finished treated and sealed tissue specimens on the supplied microscope slides 7. The camera is in a known way connected to the control unit 19 of the apparatus and the control unit is arranged to store the picture of each individual tissue specimen and information which is located on the relevant microscope slide and possibly also information about the current staining program and status of reagents at the reagents stations 3 for automatic transmission of the information to a place for result analysis.

As shown, the photo station 25 is arranged after the station 8 for application of cover glasses on the tissue specimens on the microscope slides, wherein the applying station is arranged to receive successive carriers 6 that are taking up a number of microscope slides 7 located side by side in a common plane as shown in FIG. 2. As shown, the carrier 6 in FIG. 2 is dimensioned to take up ten microscope slides.

The digital camera 26 may possibly be mounted on a microscope for making enlarged photos if the tissue specimens, or the camera may be of a type, which is especially suitable for this purpose.

The camera and the carriers 6 with the microscope slides 7 are arranged to carry out a mutual movement for location of the camera over successive microscope slides or over successive parts of a microscope slide. Thus, the camera unit may be moved over a microscope slide for taking the necessary number of pictures, or the microscope slide may be moved under the camera unit for taking the necessary number of pictures, or a combination of movements of the camera unit and the current microscope slide may be used. Generally, the camera then will be mounted on a step-by-step movable unit.

In a suitable embodiment, the movable unit may be arranged to be moved laterally in a y-direction only. In a further embodiment the apparatus comprises a transport belt for step by step movement in a x-direction of groups of microscope slides which are located side by side (in the y-direction) on the transport belt. In a supposition that it in this embodiment is needed four pictures of each microscope slide, firstly the identification field on the microscope slides in the current group will be photographed, after which the transport belt is moved approx. ¼ of the length of the microscope slide, and the camera unit is moved back for executing the same operation until the whole microscope slide and all microscope slides of the group are photographed. Then the software of the apparatus will put together the four pictures of each microscope slide tissue specimen and the identification—or information field.

The picture or pictures of the tissue specimen on microscope slides, all information on the belonging label on the microscope slide and also information about which staining program this microscope slide has gone through and status of the reagents can automatically be stored in the microprocessor which is included in the control unit of the apparatus, or possibly in a connected server. Thus, this information can automatically be loaded and without unnecessary time delay to the place where the result analysis (the screening) is carried out. Thus, the specimen can be analysed on a display by a pathologist. The pathologist may e.g. be localized in another building or another place in the world, and the picture information can be transmitted via e.g. the Internet. By possible problems with the reading etc., a local pathologist may in any case receive the tissue specimen slide for an ordinary screening under microscope. Today it also exists software which helps the pathologists by localizing "problem areas" in a tissue specimen and which may present a preliminary diagnosis. It is likely that this technology will be considerably better and faster in the future.

A photo station of the above-mentioned type can be used on conventional staining machines and on so called immune staining machines where a cover glass or a film is placed on the tissue specimen slide so that a picture can be taken.

The invention claimed is:

1. A method for automatic staining of tissue specimens on microscope slides, the method comprising:
    providing a stainer comprising treatment stations for staining of tissue specimens on microscope slides, the stainer comprising:
        two or more staining stations configured to stain the tissue specimens on the microscope slides;
        a cover-glass application station configured to automatically mount cover glasses on the stained tissue specimens on the microscope slides; and
        a photo station comprising a camera mounted on a microscope and a background light source;
    selecting a staining program to execute at least one operation in connection with staining of the tissue specimens; and
    taking one or more back lit photomicrographs of the stained tissue specimens on the microscope slides.

2. The method of claim 1, further comprising providing a conveyor in the stainer to transport the microscope slides between the two or more staining stations in accordance with the staining program.

3. The method of claim 1, further comprising mounting the photo station on a step by step movable unit arranged for positioning the microscope over successive microscope slides, or over successive parts of a microscope slide.

4. The method of claim 3, comprising moving the movable unit laterally in a y-direction.

5. The method of claim 1, further comprising providing a transport belt in the stainer for step-by-step movement of the microscope slides in a x-direction.

6. The method of claim 1, further comprising providing a control unit in the stainer, the control unit having a microprocessor configured to control the execution of the at least one operation.

7. The method of claim 6, comprising transmitting information about the staining program and a status of one or more reagents in the staining stations to the remote analysis unit.

8. The method of claim 1, comprising storing the photomicrographs of the stained tissue specimen in the control unit.

9. The method of claim 1, comprising transmitting the photomicrographs of the stained tissue specimen to a remote analysis unit for further processing.

10. The method of claim 1, further comprising detecting when microscope slides arrives at the cover-glass application station and automatically mounting cover glasses on the stain tissue specimens on the microscope slides.

* * * * *